US007364920B2

(12) United States Patent
Braun et al.

(10) Patent No.: US 7,364,920 B2
(45) Date of Patent: Apr. 29, 2008

(54) METHOD FOR GOLD DEPOSITION

(75) Inventors: Erez Braun, Haifa (IL); Yoav Eichen, Haifa (IL); Uri S. Sivan, Haifa (IL)

(73) Assignee: Technion Research and Development Foundation Ltd., Haifa (IL)

( * ) Notice: Subject to any disclaimer, the term of this patent is extended or adjusted under 35 U.S.C. 154(b) by 0 days.

(21) Appl. No.: 11/314,154

(22) Filed: Dec. 21, 2005

(65) Prior Publication Data

US 2006/0211136 A1  Sep. 21, 2006

Related U.S. Application Data

(63) Continuation of application No. 09/830,457, filed as application No. PCT/IL99/000570 on Oct. 27, 1999, now Pat. No. 7,056,748.

(51) Int. Cl.
*G01N 33/553* (2006.01)

(52) U.S. Cl. .................................... 436/525

(58) Field of Classification Search ............... 436/518, 436/524, 525, 73, 80, 84, 164, 546, 805, 436/547, 548, 6, 7.5
See application file for complete search history.

(56) References Cited

U.S. PATENT DOCUMENTS

| | | | |
|---|---|---|---|
| 3,032,436 A | 5/1962 | Gostin et al. | |
| 3,833,894 A | 9/1974 | Aviram et al. | |
| 4,314,821 A | 2/1982 | Rice | |
| 4,822,566 A | 4/1989 | Newman | |
| 5,063,417 A | 11/1991 | Hopfield | |
| 5,089,545 A | 2/1992 | Pol | |
| 5,137,827 A | 8/1992 | Mroczkowski et al. | |
| 5,202,151 A | 4/1993 | Ushio et al. | |
| 5,283,174 A | 2/1994 | Arnold et al. | |
| 5,284,748 A | 2/1994 | Mroczkowski et al. | |
| 5,312,527 A | 5/1994 | Mikkelsen et al. | |
| 5,445,934 A | 8/1995 | Fodor et al. | |
| 5,491,098 A * | 2/1996 | Noppe et al. ............... | 436/525 |
| 5,561,071 A | 10/1996 | Hollenberg et al. | |
| 5,563,424 A | 10/1996 | Yang et al. | |
| 5,653,939 A | 8/1997 | Hollis et al. | |
| 5,679,519 A | 10/1997 | Oprandy | |
| 5,707,845 A | 1/1998 | Ueyama et al. | |
| 5,739,308 A | 4/1998 | Kandimalla et al. | |
| 5,770,369 A | 6/1998 | Meade et al. | |
| 5,787,032 A | 7/1998 | Heller et al. | |
| 5,787,332 A | 7/1998 | Black et al. | |
| 5,824,473 A | 10/1998 | Meade et al. | |
| 5,837,546 A | 11/1998 | Allen et al. | |
| 5,858,659 A | 1/1999 | Sapolsky et al. | |
| 5,871,918 A | 2/1999 | Thorp et al. | |
| 5,874,046 A | 2/1999 | Megerle | |
| 5,876,976 A | 3/1999 | Richards et al. | |
| 5,891,630 A | 4/1999 | Eggers et al. | |
| 5,914,505 A | 6/1999 | Hisada et al. | |
| 5,946,550 A | 8/1999 | Papadimitrakopoulos | |
| 5,993,632 A | 11/1999 | Becker et al. | |
| 6,051,380 A | 4/2000 | Sosnowski et al. | |
| 6,060,023 A | 5/2000 | Maracas | |
| 6,071,699 A | 6/2000 | Meade et al. | |
| 6,093,370 A | 7/2000 | Yasuda et al. | |
| 6,210,880 B1 | 4/2001 | Lyamichev et al. | |
| 6,306,584 B1 | 10/2001 | Bamdad | |
| 6,391,558 B1 | 5/2002 | Henkens et al. | |
| 6,399,303 B1 | 6/2002 | Connolly | |
| 6,506,564 B1 * | 1/2003 | Mirkin et al. .............. | 435/6 |
| 6,602,669 B2 | 8/2003 | Letsinger et al. | |
| 6,645,721 B2 | 11/2003 | Mirkin et al. | |
| 6,670,113 B2 | 12/2003 | Hainfeld | |
| 6,946,675 B2 | 9/2005 | Braun et al. | |
| 2002/0137070 A1 | 9/2002 | Mirkin et al. | |
| 2002/0137071 A1 | 9/2002 | Mirkin et al. | |
| 2002/0137072 A1 | 9/2002 | Mirkin et al. | |
| 2002/0146720 A1 | 10/2002 | Mirkin et al. | |
| 2002/0155462 A1 | 10/2002 | Mirkin et al. | |
| 2002/0160381 A1 | 10/2002 | Mirkin et al. | |
| 2002/0164605 A1 | 11/2002 | Mirkin et al. | |
| 2002/0182608 A1 | 12/2002 | Connolly | |
| 2003/0022169 A1 | 1/2003 | Mirkin et al. | |
| 2003/0044805 A1 | 3/2003 | Mirkin et al. | |
| 2003/0049630 A1 | 3/2003 | Mirkin et al. | |
| 2003/0054358 A1 | 3/2003 | Mirkin et al. | |
| 2003/0059777 A1 | 3/2003 | Mirkin et al. | |
| 2003/0068622 A1 | 4/2003 | Mirkin et al. | |
| 2003/0087242 A1 | 5/2003 | Mirkin et al. | |
| 2003/0180783 A1 | 9/2003 | Mirkin et al. | |

FOREIGN PATENT DOCUMENTS

| | | |
|---|---|---|
| EP | 0 364 208 A1 | 4/1990 |
| EP | 0 426 300 A1 | 5/1991 |
| EP | 0 444 840 A1 | 9/1991 |
| JP | 04/148669 | 5/1992 |
| WO | WO 90/05300 | 5/1990 |

(Continued)

OTHER PUBLICATIONS

Ackley et al., "DNA Technical for Optoelectronics," *IEEE*, (1998).
Alivisatos et al., "Organization of 'Nanocrystal Molecules' Using DNA," *Nature*, 382;609-611 (1996).
Averin et al., in Altshuler, eds., "Single Electronics: A Correlated Transfer of Single Electrons and Cooper Pairs in Systems of Small Tunnel Junctions," *Mesoscopic Phenomena in Solids*, New York, New York: Elsevier Science Publishing Company, Inc., 173-271 (1991).

(Continued)

*Primary Examiner*—Ann Y. Lam
(74) *Attorney, Agent, or Firm*—Volpe and Koenig, P.C.

(57) ABSTRACT

A method for depositing gold on a substrate is provided. By this aspect nucleation centers are bound, deposited or formed at one or more sites on the substrate, the substrate is then contacted with a treatment composition which comprises soluble gold-providing agent from which gold is deposited onto a nucleation center to yield gold metal deposits. The method of the invention may be used for a variety of image enhancing techniques as well as diagnostic and analyte detection techniques.

26 Claims, 6 Drawing Sheets

FOREIGN PATENT DOCUMENTS

| | | |
|---|---|---|
| WO | WO 93/25003 | 12/1993 |
| WO | WO 94/05045 | 3/1994 |
| WO | WO 97/44651 | 11/1997 |
| WO | WO 98/31839 | 7/1998 |
| WO | WO 98/53841 | 12/1998 |
| WO | WO 99/04440 | 1/1999 |
| WO | WO 99/29711 | 6/1999 |
| WO | WO 99/35256 | 7/1999 |
| WO | WO 99/36573 | 7/1999 |
| WO | WO 99/57550 | 11/1999 |
| WO | WO 99/60165 | 11/1999 |
| WO | WO 00/25136 | 5/2000 |

OTHER PUBLICATIONS

Barton, "Metal/Nucleic-Acid Interactions," in Bertini, eds., *Bioinorganic Chemistry*, Sausalito, California:University Science Books, pp. 455-503 (1994).

Bensimon et al., "Alignment and Sensitive Detection of DNA by a Moving Interface," *Science*, 265:2096-2098 (1994).

Bensimon et al., "Stretching DNA with a Receding Meniscus: Experiments and Models," *Physical Review Letters*, 74(23):4754-4757 (1995).

Bertini et al., "Bioinorganic Chemistry," *University Science Books*. 455-503 (1994).

Birrell et al., "Silver Enhanced Colloidal Gold ad a Cell Surface Marker for Photoelectron Microscopy." *Journal of Histochemistry and Ctyochemistry*, 34(3):339-345 (1986).

Braun et al., "DNA-Templated Assembly and Electrode Attachment of a Conducting Silver Wire," *Nature*, 391:775-778 (1998).

Burroughes et al., "Light-Emitting Diodes Based on Conjugated Polymers," *Nature*, 347:539-541 (1990).

Chen et al., "Synthesis from DNA of a Molecule with the Connectivity of a Cube," *Nature*, 350:631-633 (1991).

Coffer et al., "Dictation of the Shape of Mesoscale Semiconductor Nanoparticle Assemblies by Plasmid DNA," *Appl. Phys. Lett.*, 69(25):3851-3853 (1996).

Danscher et al., "Light Microscopic Visualization of Colloidal Gold on Resin-Embedded Tissue," *Journal of Histochemistry and Cytochemistry*, 31(12):1394-1398 (1983).

Danscher, "Localization of Gold in Biological Tissue. A Photochemical Method of Light and Electronicroscopy," *Histochem.*, 71:81-88 (1981).

Demitras et al., "An Extension of the Role of O(2) of Cytosine Residues in the Binding of Metal Ions, Synthesis and Structure of an Unusual Polymeric Silver(I) Complex of l-Methylcytosine," *J. Am. Chem. Soc.*, 99(8):2797-2798 (1977).

Du et al., "Synthesis of a SNA Knot Containing Both Positive and Negative Nodes," *Journal of American Chemical Society*, 114(24):9652-9655 (1992).

Eichhorn, "Complexes of Nucleosides and Nucleotides," in Eichhorn, ed., *Inorganic Biochemistry*, vols. 1 and 2, New York, New York:American Elsevier Publishing Company, pp. 1191-1243 (1973).

Fink et al., "Electrical Conduction Through DNA Molecules," *Nature*, 398:407-410 (1999).

Goffeau, "Molecular Fish on Chips," *Nature*, 385:202-203 (1997).

Grabar et al., "Kinetic Control of Interparticle Spacing in Au Colloid-Based Surfaces: Rational Nanometer-Scale Architecture," *J. Am. Chem. Soc.*, 118:1148-1153 (1996).

Hall et al., "Oxidative DNA Damage Through Long-Range Electron Transfer," *Nature*, 382:731-735 (1996).

Hiroaki, "Spherical fine gold parricle prodn. For ceramics or electronic industry", Apr. 27, 1993, XP-002129601.

Holgate et al., "Immunogold—Silver Staining," *Journal of Histochemistry and Cytochemistry*, 31(7):938-944 (1983).

Kallenbach et al., "An Immobile Nucleic Acid Junction Constructed from Oligonucleotides," *Nature*, 305:829-831 (1983).

Kastner et al., "The Single Electron Transistor," *Reviews of Modern Physics*, 64(3):849-858 (1992).

Klein et al., "An Approach to Electrical Studies of Single Nanocrystals," *Appl. Phys. Lett.*, 68(18):2574-2576 (1996).

Kouwenhoven et al., "Introduction to Mesoscopic Electron Transport," in Sohn, eds., *Mesoscopic Electron Transport*, The Netherlands:Kluwer Academic Publishers, pp. 1-44 (1997).

Langer et al., "Quantum Transport in a Multiwalled Carbon Nanotube," *Physical Review Letters*, 76(3):479-482 (1996).

Meirav et al., "Single Electron Phenomena in Semiconductors," *Semiconductor Science Technology* 11:255-284 (1996).

Mirkin et al., "DNA-Based Method for Rationally Assembling Nanoparticles into Macroscopic Materials," *Nature*, 382:607-609 (1996).

Mueller et al., "Design and Synthesis of a Knot From Single-Stranded DNA," *Journal of American Chemical Society*, 113(16):6306-6308 (1991).

Porath et al., "Single Electron Tunneling and Level Spectroscopy of Isolated $C_{60}$ Molecules," *J. Appl. Phys.*, 81 (5):2241-2244 (1997).

Roberts et al., "A New Procedure for the Detection of Gold on Animal Tissue," *Proceedings of the Section of Sciences*, N. V. Noord-Hollandsche Uitgeversmaatschappij, Amsterdam, 38:540-544 (1935).

Sato et al., "Single Electron Transistor Using a Molecularly Linked Gold Colloidal Particle Chain," *J. Appl. Phys.*, 82(2):696-701 (1997).

Scopsi et al., "Colloidal Gold Probes in Immunocytochemistry. An Optimization of Their Application in Light Microscopy by Use of Silver Intensification Procedures," *Med. Biol.*, 64:139-145 (1986).

Scopsi et al., "Increased Sensitivity in Immunocytochemistry. Effects of Double Application of Antibodies and of Silver Intensification on Immunogold and Peroxidase-Antiperoxidase Staining Techniques," *Histochemistry*, 82:321-329 (1985).

Seeman et al., "Synthetic DNA Knots and Catenanes," *New Journal of Chemistry*, 17(10):739-755; 1993.

Size, *Physics of Semiconductor Devices*, $2^{nd}$ Ed., 349:490-495 date unknown.

Springall et al., "The Potential of the Immunogold-Silver Staining Method for Paraffin Sections," *Histochemistry*, 81:603-608 (1984).

Teasdale et al., "Identification of Oestrogen Receptors in Cells of Paraffin-Processed Breast Cancers by IGSS," *Histochemistry*, 87:185-187 (1987).

Wirtz, "Direct Measurement of the Transport Properties of a Single DNA Molecule," *Physical Review Letters*, 75(12):2436-2439 (1995).

Zimmermann et al., "DNA Stretching on Functionalized Gold Surfaces," *Nucleic Acids Research*, 22(3):492-497 (1994).

B.L. Altshuler et al., "Mesoscopic Phenomena in Solids", Elsevier Science Publishers, B.V., 1991, pp. 176-271.

L.G. Marzilli et al., "An Extension of the Role of O(2) of Cytosine Residues in the Binding of the Metal Ions, Synthesis and Structure of an Unusual Polymeric Silver(I) Complex of 1-Methylcytosine,"Journal of the American Chemical Society, 99:8, Apr. 13, 1977 (2 pages).

Gorm Danscher et al., "Light Microscopic Visualization of Colloidal Gold on Resin-Embedded Tisuee", The Journal of Histochemistry and Cytochemistry, vol. 31, No. 12, 1983, pp. 1394-1398.

Nadrian C. Seeman, et al., "Synthetic DNA Knots and Catenanes", New Journal of Chemistry, vol. 17, No. 10-11-1993.

* cited by examiner

METHOD FOR GOLD DEPOSITION

CROSS-REFERENCE TO RELATED APPLICATION

This application is a continuation of co-pending application 09/830,457, filed Oct. 9, 2001, which was a 371 National Phase Entry of co-pending International Application No. PCT/IL1999/000570, filed Oct. 27, 1999, which designated the U.S. and which claims the benefit under 35 U.S.C. § 119 of Israel Application No. IL 126776, filed Oct. 27, 1998.

FIELD OF THE INVENTION

The invention relates to chemical deposition of gold metal on substrates.

BACKGROUND OF THE INVENTION

There are various techniques and uses in which metal substances are deposited on substrates. In various such methods, the metal to be deposited is provided in a form of a soluble complex or molecule, e.g. in an aqueous solution. Under appropriate conditions the complex or molecule is reduced and deposits the metal onto the substrate.

At times, in order to ensure deposition of metal from solution onto a substrate, it is preferable to first provide nucleation centers on the substrate. Such nucleation centers may, for example, be a variety of metal complexes, clusters or small metal particles, deposited on or attached to the surface.

Examples of techniques involving metal deposition are a variety of image formation or latent image contrast-enhancement techniques for photography, optical microscopy or electron microscopy. Another example of laboratory techniques where metal complexes are deposited onto a substrate, is in imaging of separation products, e.g. proteins or nucleic acids, in a variety of chromatographic or electrophoretic techniques.

The metal most typically used in such techniques is silver. However, one typical drawback of silver deposition is that the deposition is not completely specific and some degree of spontaneous deposition of silver may occur also without an a priori deposition of nucleation centers. Thus, where silver deposition is used in image-enhancement or contrast-enhancement methods, there is typically a limited signal-to-noise ratio.

GENERAL DESCRIPTION OF THE INVENTION

The present invention has, as one of its objects, the provision of a method for depositing gold onto specific sites on a substrate. Another object of the invention is to provide a composition and kit for use in such a method.

In accordance with the present invention gold, initially contained in a soluble gold-providing agent, being a gold-containing molecule, cluster or complex, is deposited onto nucleation centers. The term "nucleation centers" as used herein refers to any salt, complex, cluster or particle having catalytic properties of transforming gold from a gold-containing molecule or complex into gold metal. Particles with a metal surface are, for example, colloid metal particles, a variety of metal complexes, clusters containing metal atoms, etc.

In accordance with the invention there is provided a method for depositing gold at one or more sites on a substrate, comprising:

(a) binding, depositing or forming nucleation centers at said one or more sites;

(b) contacting said one or more sites with a treatment composition comprising said gold-providing agent and a reagent, the composition being kinetically stable such that gold metal is essentially not deposited on the substrate unless a nucleation center is present on the substrate and in the presence of a nucleation center at said one or more sites, gold atoms are released from said gold-providing agent and deposited onto said nucleation center to form gold metal deposits at said one or more sites.

As will be appreciated, once gold is deposited on the substrate, it serves as a nucleation center for further gold deposition. By appropriately controlling the incubation time as well as other conditions affecting the gold deposition (some of which will be outlined bellow), the amount of the deposited gold at a deposition site can be controlled. Furthermore, although the initial gold deposition may be at discrete sites on the substrate, by allowing the gold deposits to grow, following further deposition, discrete sites may combine to form one larger gold deposit encompassing the so combined sites.

The term "essentially not deposited" means to denote that there is either no gold separation from the solution and the gold atoms remain within the soluble molecule or complex, or that gold metal deposition on a substrate is negligible and thus not or only hardly observable and measurable, yielding a high signal-to-noise ratio.

In accordance with one embodiment, the nucleation centers are formed by chemical or physical deposition of nucleation center forming agent onto the one or more sites. By another embodiment, such nucleation centers may be formed chemically at said one or more sites by a redox reaction in which metal ions, in particular silver ions, are oxidized into metallic silver. Such chemical formation of nucleation centers is known per se (see for example WO 99/04402 and PCT/IL99/00232).

In accordance with yet another embodiment, the nucleation centers are formed by binding of nucleation center-forming agents at said one or more sites. Such agents comprise at least one binding moiety with a binding affinity (which may be specific or non-specific) to said one or more sites, which is bound to at least one nucleation center moiety. The nucleation center moiety is a species that can act as a catalytic agent for gold metal deposition, e.g. a salt, metal particle, cluster of metal atoms or a metal-containing complex. The binding moiety may, for example, be one member of a recognition group, where another member of the recognition group forms or is included in said one or more sites. The recognition group, typically a recognition couple, consists of two or more substances with a binding affinity one to the other. The recognition group may be, but is not limited to, any one of the following couples: an antigen and an antibody or an antibody derivative with a complementary antigen-binding domain; sugar and a lectin; a receptor and a ligand; a nucleotide sequence and a complementary nucleotide sequence; a nucleotide sequence and its binding protein or synthetic binding agent; biotin and avidin or streptavidin; cellulose or chitin and cellulose binding domain.

The nucleation center moiety is preferably a gold particle or a cluster containing gold atoms, e.g. $Au_{11}$ or $AU_{55}$ or $Au_{147}$ (gold clusters that contain 11, 55 or 147 gold atoms, respectively). The treatment composition is typically an aqueous solution. Said gold-providing agent is preferably a gold complex such as $Au^I(SCN)_2^-$ usually in the form of an alkali metal (e.g. $Na^+$ or $K^+$) or ammonium salt.

The reagent in the treatment composition may be a reducing agent. Where said gold-providing agent is $Au^I(SCN)_2^-$ the reagent is preferably a quinone, e.g. hydroquinone (HQ) or naphtohydroquinone (NHQ). However, any other agent which can reduce a gold-containing molecule or complex to obtain gold metal, but because of kinetic limitations (e.g. high activation energy and low pre-exponential factor) will do so in a negligible rate in the absence of a nucleation center, yet, in a meaningful rate (namely in a rate that yields observable results in a not too long period of time) when a nucleation center is present, may also be used.

A treatment composition comprising $Au^I(SCN)_2^-$ and HQ in an acidic medium is stable, meaning that gold remains as soluble species in solution and neither precipitates as solid metal nor is deposited on solid substrates other than nucleation centers. When the pH of such a treatment composition is below about 6, the treatment composition is particularly stable. Upon contact with a nucleation center gold metal is deposited on sites of the substrate comprising nucleation centers.

The rate of deposition of the gold metal may be controlled, for example, by controlling the pH of the treatment composition: increase in pH will increase the rate of gold deposition and a decrease in pH will decrease the deposition rate. Furthermore, the rate of deposition may also be controlled by a variety of other means, for example: by controlling the flow parameters of the treatment composition (rapid flow prevents poisoning by by-products, such as $CN^-$, which can reduce the rate of gold deposition); by adding surface active agents which can either increase or decrease the rate of deposition (for example polyamines, poly acids or polyalcohols and other surface active agents may have the effect of altering the rate of gold deposition). In addition, by the use of various additives, e.g. those noted above, the roughness of the surface of the deposited gold may be changed (such a change may result in a change of color and electrical properties of the deposited gold).

The method of the invention may be used for assaying the presence or concentration of a specific substance at sites on a substrate. Such a method comprises the following steps:

(a) providing conditions allowing formation of nucleation centers on sites containing said substance;

(b) contacting said substrate with a treatment composition comprising said gold-providing agent and a reagent, the composition being kinetically stable such that upon such exposure gold metal is essentially not deposited on the substrate unless a nucleation center is present thereon, and in the presence of a nucleation center at said sites, gold atoms are released from said gold-providing agent and deposited onto said nucleation centers to form gold metal at said sites; and (c) detecting gold deposits on said substrate, a gold deposit at a site on the substrate indicating presence of said substance at said site.

The assay method may be applicable, for example, in a variety of assay techniques, e.g. in techniques involving visualization of specimens in microscopy (which may be an optical or an electron microscope) or any SPM (_____) technique, or in identifying specific separation products on a substrate (for example, a separation product of electrophoresis or chromatography contained in a gel or on a solid substrate such as DNA-chip). In such an assay, the nucleation centers may be formed by the use of said nucleation center-forming agents where the moiety with the specific binding affinity is one member of a recognition group, which may be any of those mentioned above, and the agent to be assayed is another member of the group.

In accordance with another embodiment, the gold deposition method of the invention is used in an assay intended to detect the presence of an analyte in a sample. In particular, the present invention is applicable to such a method where a capturing agent held on a substrate is used to detect the presence of an analyte in a sample that binds specifically to the capturing agent. Such a capturing agent may be a member of a recognition group, while the analyte is another member of the group. A specific example is the case of assaying for the presence of a target oligonucleotide in a sample, with the capturing agent being an oligonucleotide with a sequence complementary thereto. A nucleation center forming moiety may be bound to analytes presence in the sample, e.g. to the oligonucleotides in the sample, and then after allowing the sample to react with the substrate, and performing a gold deposition reaction as described above, formation of gold deposits will indicate the presence of the analyte in the sample.

A method of the invention of preparing a specimen for imaging in a microscope, comprises the following steps:

(a) providing conditions permitting formation of nucleation centers at selective sites of the specimen; and (b) contacting said specimen with a treatment composition comprising said gold-providing agent and a reagent, the composition being kinetically stable such that gold is essentially not deposited on the specimen unless a nucleation center is present thereon, whereby gold atoms from said gold-providing agent are released and deposited onto said specimen at said selective sites.

A method of the invention for detecting the presence of an analyte in a sample, comprises the following steps:

(a) treating the sample to bind nucleation center forming moieties to the analyte, if present in the sample;

(b) reacting the sample with a substrate, holding capturing agents that specifically bind said analyte, and removing unbound sample portions;

(c) contacting said substrate with a treatment composition comprising said gold-providing agent and a reagent, the composition being kinetically stable such that upon such exposure gold metal is essentially not deposited on the substrate unless a nucleation center is present thereon, and in the presence of a nucleation center at said sites, gold atoms are released from said gold-providing agent and deposited onto said nucleation centers to form gold metal at said sites; and (d) detecting gold deposits on said substrate, a gold deposit indicating presence of the analyte in the sample.

A specific application of this method is in the oligonucleotide chips. Oligonucleotide chips have different capturing oligonucleotides deposited in different sites on the chip. Applying the above method may allow to simultaneously assay for a large number of different oligonucleotides in a sample.

In a so prepared specimen, said selective sites thus contain gold deposits which permit their visualization. Said selective sites may typically be sites containing a specific substance and the nucleation centers are then formed at said sites by nucleation center forming agents with a moiety having specific binding affinity to said specific substance. In this manner, for example, specific cells, organelles, regions rich with a specific substance, etc. can be clearly visualized.

A method according to the invention for identifying locations of a specific separation product on a substrate, comprises the following steps:

(a) providing conditions permitting formation of nucleation centers at sites on said substrate comprising said specific separation product;

(b) contacting said substrate with a treatment composition comprising said gold-providing agent and a reagent, the composition being kinetically stable such that gold is deposited on the substrate essentially only where a nucleation center is present thereon, whereby upon such contact, gold atoms from said gold-providing agent are released and deposited onto said nucleation center to form gold metal; and (c) detecting presence of gold on said substrate, such gold signifying presence of said specific separation product on the substrate at a site where the gold is detected.

In a separation technique where the sample is separated into various fractions based on different movement rates of different substances through a medium (typically a gel or a solid) under applied conditions, for example electrophoresis, thin layer chromatography (TLC), etc., the nucleation centers-forming agents may be admixed to the sample prior to separation. This is usually preferred. For one such prior addition of the nucleation center-forming agent may be more economical, as less material may be required. In addition, where such agents are applied to the substrate after the separation, they have to diffuse through the medium in order to reach the separated substance located within the medium; such diffusion may be a limiting factor in proper gold-staining of separated fractions. However as will readily be appreciated, it is possible at times to add the nucleation center-forming agent also after separation.

The present invention also provides a method for assaying presence of an analyte in a sample. Such a method comprises the following steps:

(a) providing a substrate carrying capturing agents which bind said analyte;

(b) contacting said substrate with said sample, whereby said analyte binds to said capturing agents;

(c) providing conditions permitting formation of nucleation centers on sites of said substrate comprising said analyte;

(d) contacting said substrate with a treatment composition comprising said gold-providing agent and a reagent, the composition being kinetically stable such that gold is deposited on the substrate essentially only at sites thereof containing the nucleation centers; and (e) detecting metallic gold deposits on said substrate, indicative of the presence of said analyte in said sample.

The detection in step (e) of the method for assaying presence of an analyte in a sample, may be carried out by testing appearance of gold deposited on the substrate (gold deposited, depending on size and roughness, may have a color ranging from yellow to orange to red).

In accordance with one embodiment of the invention, the detection in step (e) is based on the electric conductivity of the deposited gold. In this embodiment the capturing agents may be carried on the substrate between electrodes or may be carried on one or more electrodes such that the gold deposited onto the nucleation center in step (d) establishes an electric contact between electrodes. The detection of the gold deposits in step (e) is thus carried out by determining existence of electrical contact between the electrodes, e.g. by measuring the current-potential relationship between the electrodes. The magnitude of the current-potential relationship may be used as a gauge for the agent's concentration in the sample. Alternatively, determining the number of connections in a large array of similar electrode couples with identical capturing agents carried between or on them, may also provide a quantitative measure of the analyte concentration.

The assayed analyte may be a member of any of the recognition couples mentioned above, with the other member of the couple being then included as a moiety in the capturing agent. The formation of the nucleation centers in step (c) may be the provision of agents having a binding moiety with specific binding affinity to the analyte captured on the substrate by the capturing agent, bound to a nucleation-forming moiety, which may be a metal particle, a cluster containing metal atoms or a metal-containing complex, or any other species having the catalytic properties of transforming gold-containing molecular species into gold metal. For example, where the analyte is one member of a binding couple, the binding moiety may be another member (e.g. where the analyte is an antigen, the nucleation center-forming agent may comprise an antibody, which may be the same or different as an antibody used as the capturing agent).

The present invention further provides a kit for use in the above method. Such a kit typically comprises a treatment composition. In addition, such a kit may also comprise a reagent for forming nucleation centers at specific sites on a substrate, e.g. such having a specific binding moiety being a member of any of the above binding couples. In addition, a kit for use in the above assay method may also comprise, according to some embodiments, a reagent system for tagging an analyte in a sample with nucleation center-forming moiety. Furthermore, in accordance with some embodiments of the invention, the kit may comprise a substrate comprising electrodes with capturing agents disposed between and/or on the electrodes.

In order to understand the invention and to see how it may be carried out in practice, a preferred embodiment will now be described, by way of non-limiting example only, with occasional reference to the accompanying drawings.

DETAILED DESCRIPTION OF A PREFERRED EMBODIMENT

Preparation of a Treatment Composition and General Gold Deposition Scheme

A treatment composition in accordance with the preferred embodiment of the invention comprises a gold-containing complex-$Au^I SCN^-$. In order to prepare such a treatment composition at a first stage a solution comprising $KAu^{III}Cl_4$ and KSCN is prepared, typically by mixing two stock solutions, one comprising the gold containing complex and the other the KSCN. For example, such a solution may be formed by mixing equal volumes of a first solution comprising about 0.5 M KSCN and a second solution comprising about 0.05 M $KAu^{III}Cl_4$. Such mixing results in the formation of the complex $KAu^{III}(SCN)_4$ (See Scheme (a) in FIG. 1). This complex precipitates but spontaneously forms the complex $KAu^{I}(SCN)_2$. Typically, after the $KAu^{III}(SCN)_4$ is precipitated, it is washed and resuspended in water or buffer and allowed to undergo the spontaneous reaction (SPONT.) noted above (illustrated in Scheme (b) of FIG. 1).

The $KAu^{I}(SCN)_2$ solution is then mixed with a reducing agent, e.g. with about 0.055 M hydroquinone (HQ). The reduction of the gold-containing complex by the hydroquinone is then thermodynamically favorable, but owing to the large activation energy and low pre-exponential factor, the kinetics is very slow. At a pH of less than about 6, the spontaneous reduction is practically nil. Thus, the solution is stable and gold metal is not deposited spontaneously.

Figure 1:
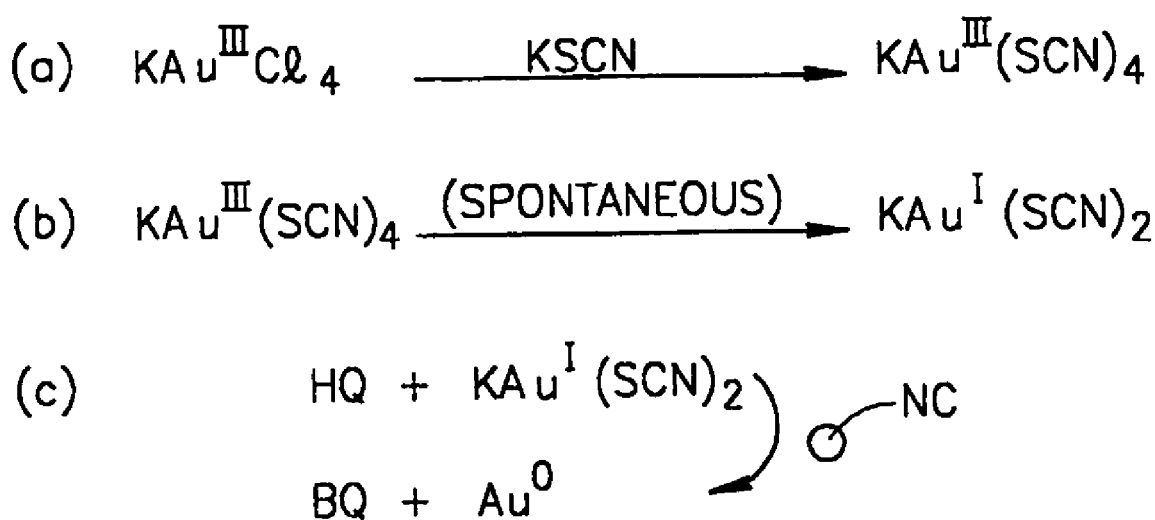
FIG. 1 shows reaction schemes of the manner of preparation of a treatment composition in accordance with an embodiment of the invention (Scheme (a) and Scheme (b)) and of gold deposition onto a nucleation center (Scheme (c)).

However, as shown in FIG. 1, scheme (c), upon exposure to nucleation centers (NC), acting as catalysts, which may for example be gold colloids, other metal colloids, clusters of metal atoms, metal-containing complexes, metal ions, etc., gold metal ($Au^0$) is being deposited on the surface of the nucleation center associated with the formation of benzoquinone (BQ).

The pH level controls the rate of gold deposition: acidification of the solution, namely lowering pH, slows the metal deposition, while addition of a base, namely increasing pH, accelerates the rate of metal deposition.

It should be noted that under basic pH, some spontaneous deposition of gold may take place even without nucleation centers.

Various additives which may either be added initially to the treatment solution, or added during the deposition process, may influence the rate of the gold deposition process and the pattern of the gold deposit (size of deposits, surface roughness, color, etc.). For example, addition of halogen ions to the treatment composition results in surface poisoning of the growing metal centers. This will reduce the rate, and eventually stop the gold deposition process. Use of such additives thus allows a control of the deposited gold crystalinity, grain size, the rate of the gold deposition, the roughness of the surface of the deposited gold, the electrical properties, etc. The gold deposition process may obviously also be controlled by the change of various other parameters such as temperature, oxygen content, light flux, solution-agitation rate, etc.

The gold deposition process of the invention can be used for a variety of diverse applications, some examples of which will be illustrated below.

Detection of Analytes in a Sample

Figure 2:
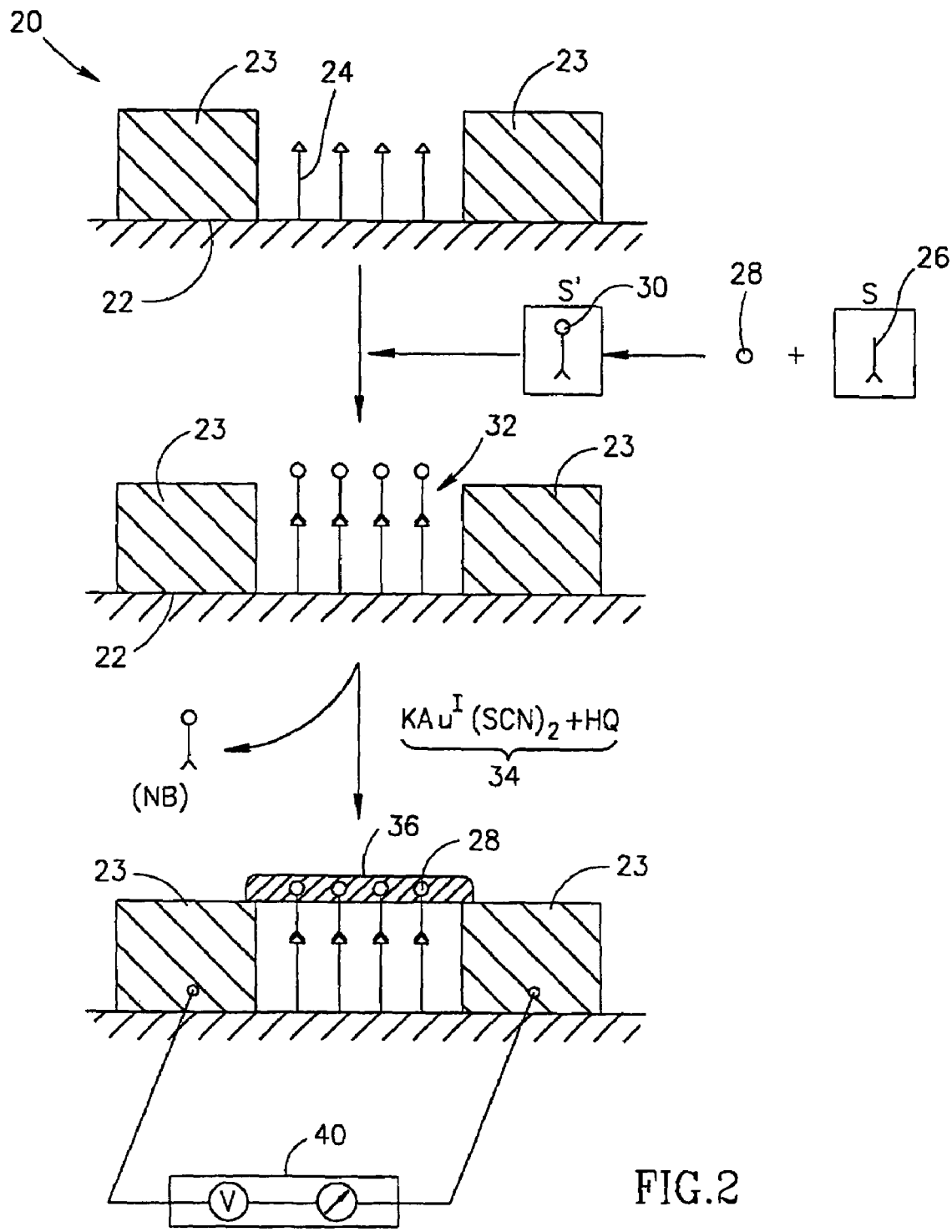
FIG. 2 is a schematic representation of an assay of an analyte in a sample in accordance with an embodiment of the invention.

An assay in accordance with one embodiment of the invention is illustrated in FIG. 2. Provided by this embodiment is a device 20 having a non conductive substrate 22 carrying electrically conductive electrodes 23. In the gap between electrodes the substrate 22 carries capturing agents 24 which have a specific binding affinity to analyte 26 to be assayed.

Sample S, which comprises analyte 26, is pretreated by adding nucleation centers 28 and treating it in a manner so that nucleation centers will become coupled to the analyte in a covalent or non covalent interaction, to yield modified analyte 30. In the case of an oligonucleotide analyte, such coupling may, for example, be performed by heating the sample in the presence of a cis-platinum-biotin and then adding an appropriately derivatized cluster, e.g. $Au_{55}(Ph_3P)_{12}Cl_6$-streptavidin cluster. The cis-platinum-biotin binds to the oligonucleotides, then $Au_{55}(Ph_3P)_{12}Cl_6$-streptavidin binds to the biotin moieties on said nucleotides, thus binding nucleation moieties to the analyte. In the case of a non-nucleotide analyte, coupling may be achieved, for example by binding amino-derivatized cluster or colloid to carboxy moieties of the analyte; coupling carboxy-derivatized clusters or colloids to amino-moieties of the analyte; coupling maleimido-derivatized cluster or colloids to thiol moieties of the analyte; etc. As will be appreciated, other substances in a sample may also become tagged with the nucleation center in this process. However, these will not bind to capturing agents 24 and the nucleation centers coupled thereto will thus not remain on the substrate after treatment. (See description below).

Upon contact with device 20, modified analyte 30 binds to the capturing agents to yield nucleation center-forming complexes 32 which are immobilized on substrate 22. Washing the substrate removes unbound substances (NB).

Device 20 may then be contacted with the treatment solution 34 which comprises a gold containing complex such as $KAu^{I}(SCN)_2$ and a reducing agent such as hydroquinone (HQ) and consequently upon contact with the nucleation centers 28, gold is deposited on the nucleation centers and forms a continuous gold mass 36 extending between electrodes 23. In order to avoid that electrodes 23 will act as nucleation centers, they may either be made of a conductive material lacking catalytic properties, e.g. silicon passivated with silica, with long alkyl chains, or passivated by coating with an inert material, or, where the electrodes are made of a metal, they may be pretreated to render them inert as gold-deposition catalysts, e.g. by incubation with a solution comprising a long chain alkane thiol, such as 1-octadecyl-thiol.

By measuring current voltage relationships using a measurement device 40, the existence of an electric contact between the electrodes 23 can be determined, the presence of which indicates the presence of the analyte in the assayed sample.

As can generally be appreciated by the artisan, the binding of the capturing agents to the substrate may be achieved in a number of ways. For example, oxide surfaces may be derivatized with a silicon reagent such as $(CH_3CH_2O)_3Si$—R—X, wherein R may be an alkyl, aryl or other spacer and X may be an active moiety for subsequent binding to a moiety Y in the capturing agent. The nature of X and Y depends on the couple and may be selected from couples consisting of acid and amine, hydroxy and acid, cycloaddition reactions, radical reactions, nucleophilic substitutions, non-covalent interactions, etc., as is well known and clear to the artisan. Where the substance is made of a polymeric material, binding, by any of the above type of reactions, or others, may also be achieved between the capturing agent and a side group of the polymeric material.

Device 20 may comprise two or more electrodes, typically a plurality of electrodes arranged in an array. The array may assume different geometries. The same capturing agents may be carried between different pairs of electrodes, and/or different capturing agents may be deposited between different electrodes. A device of the latter kind may be used in the multiplexing assay for simultaneous determination of a number of analytes. In addition, where the same capturing agents are carried between different pairs of electrodes, this may allow to perform a quantitative assay of concentration of the analyte: for example, the concentration may be assessed based on the number of electric contacts formed between different pairs of electrodes—a large number of electric contacts signifying a large concentration and a small number corresponding to a small concentration.

The electrode array may also be part of a more complex electronic setup containing different components, e.g. diodes, transistors, conductors, capacitors, etc.

Figure 3:
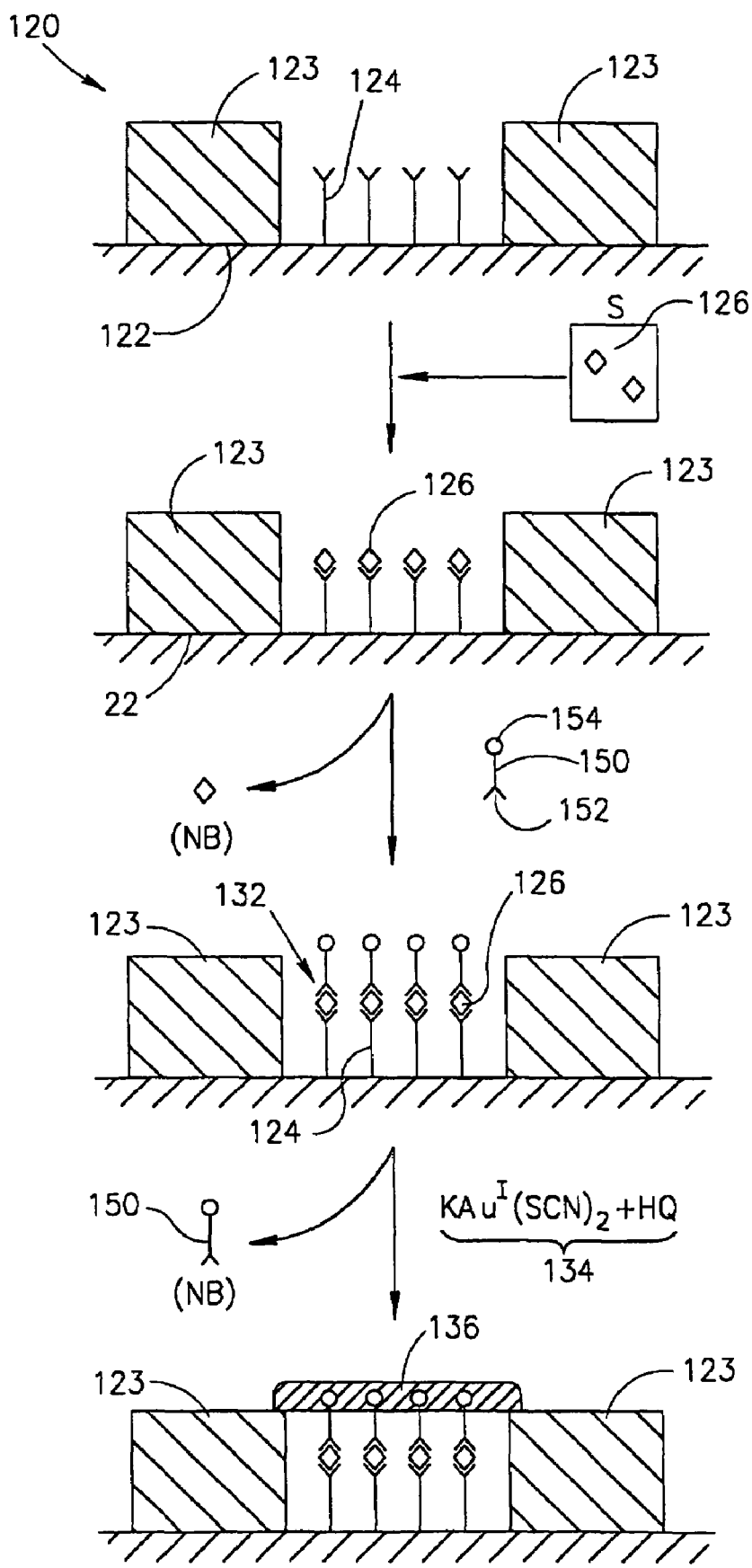
FIG. 3 is a schematic representation of an assay in accordance with another embodiment of the invention.

Another embodiment of an assay in accordance with the invention can be seen in FIG. 3. The main difference in the case of the embodiment of FIG. 3 from that described in FIG. 2, is that rather than treating sample S to bind nucleation centers 28 to analytes 26 to obtain a modified analyte 30, in the case of the embodiment of FIG. 3, a nucleation center-forming agent 150 is provided. Other components of this assay are very similar to those of FIG. 2 and thus the same reference numeral shifted by one hundred (namely with a "1" prefix) to those used in FIG. 2 were employed in FIG. 3 to indicate like components.

After contact of a device 120 with a sample, analyte 126 binds to a capturing agent 124 and then after washing free (non bound (NB)) analyte molecules and other substances in the sample, the device is contacted with a nucleation center-forming agent 150 which comprises a moiety 152 with a specific binding affinity to analyte 126 which is now bound to capturing agents 124, coupled to a nucleation center 154. Thus, an immobilized nucleation center 132 forms on the substrate in the gap between electrodes 123. Then, after removal of non bound agents 150 (NB) and adding a treatment composition 134 the gold mass 136 forms which provides electric contact between electrodes 123, which may then be determined similarly as shown in FIG. 2.

Figure 4:
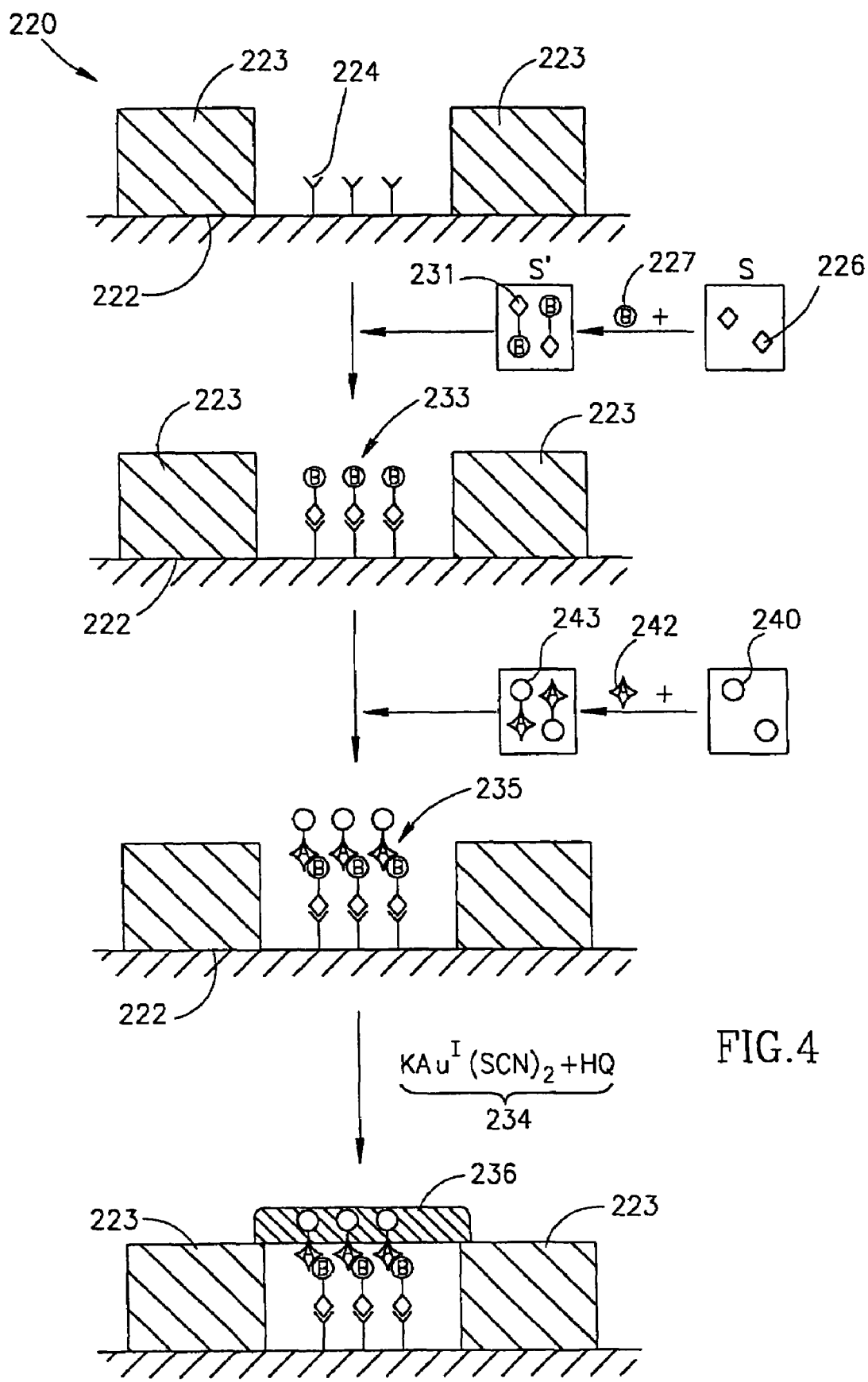
FIG. 4 is a schematic representation of an assay in accordance with a further embodiment of the invention.

A further embodiment of an assay in accordance with the invention is seen FIG. 4. In FIG. 4, like elements to those of FIGS. 2 and 3 have been marked with the same reference numeral to that used in FIG. 2 shifted by one hundred (namely with a "2" prefix). Sample S containing analyte 226 is reacted with biotin 227 to yield a treated sample S' with analyte-biotin complexes 231. These are then contacted with substrate 222 which contain capturing agents 224 fitted between electrodes 223, to yield modified capturing complexes 233 on substrate 222.

Gold colloid particles 240 are reacted with an avidin or streptavidin 242 to yield nucleation center forming agents 243. Contacting agent 243 with modified substrate 222 then yields immobilized nucleation centers 235. The subject can then be contacted with a treatment solution 234 similarly as in FIGS. 2 and 3 resulting in gold deposition to form a continuous gold mass 236 between electrodes 223.

As will no doubt be appreciated by the artisan, various modifications of the embodiments shown above are possible.

Visualization of Separation Products

Figure 5:
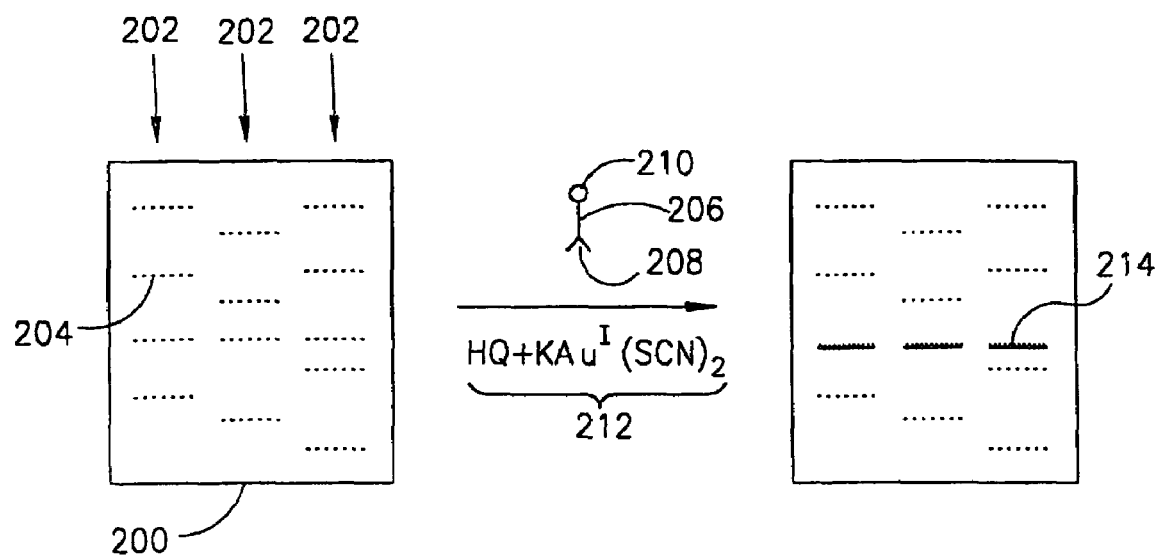
FIG. 5 is a schematic illustration of the manner of enhancing specific bands on a solid or a gel substrate, separated by chromatography or by electrophoresis.

The method of the invention can be used for visualizing separation product obtained in a number of separation techniques such as gel electrophoresis, gel permeation techniques, size exclusion chromatography, affinity chromatography and others. This is illustrated schematically in FIG. 5.

Substrate 200, which may be a gel or a solid substrate containing different lanes 202, each consisting of a plurality of bands 204, each one being a specific fraction of a sample separated in each lane. Such a substrate 200 may be obtained by any of the techniques noted above.

In order to visualize the existence of a specific substance and locate its band, a nucleation center-forming agent 206 which has a moiety 208 which specifically binds to the substance in a nucleation center 210 is contacted with substrate 200 and after access, agents 206 are washed away, the substrate is contacted with a treatment solution 212 and consequently gold deposits 214 will form on bands containing that substance (the other bands are not visible and are included only for illustration purposes). Preferably, however, nucleation center-forming agents 206 may be added to the substrate prior to the beginning of the separation process since diffusion of subsequently-added nucleation center-forming agents may be a limiting factor to achieve binding of these agents to the separated substance.

Depending on the exact deposition conditions, which will inter alia determine the roughness of the surfaces of the deposited gold mass, the color of the bands may vary between yellow to black. Using various visualization techniques, based on measurement of light absorbance or transmission through the bands, a quantitative measurement of a separate substance may be obtained.

In the alternative, rather than optical techniques, the gold deposits may also be detected by various electric detection techniques. This may be achieved for example by providing two planar arrays of electrodes sandwiching the separation matrix which will permit an automatic electric detection.

Contrast Enhancing in Imaging Techniques

There are many imaging techniques which request contrasting agents in order to view certain components. Such is the case in optical microscopy, electron microscopy (transmission electron microscopy, scanning electron microscopy) as well as in other imaging techniques, such as atomic force microscopy. Hitherto, such imaging techniques involved silver metal deposition or carbon deposition and some others.

In the case of biological specimens, contrast enhancers are required to allow visualization of specific tissues, cells, organelles, etc.

Figure 6:
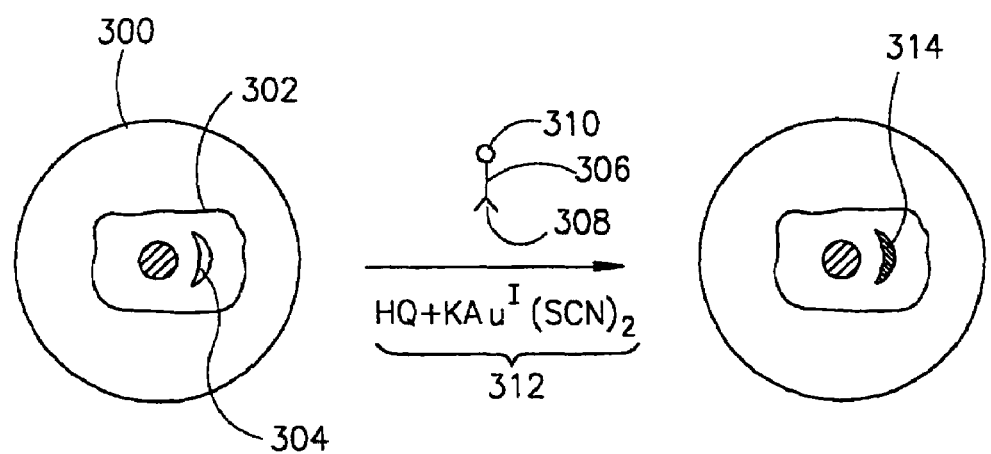
FIG. 6 is a schematic illustration of a method in accordance with an embodiment of the invention for imaging specific parts of a microscope specimen.

In accordance with the invention, as illustrated in FIG. 6, a biological specimen 300, containing a cell 302 with a non visible organelle 304, is treated in accordance with the invention by successive exposure to nucleation center-forming agent 306 which has a binding moiety 308 specific to substance included in organelle 304 and a nucleation center 310 and after treatment with a treatment composition 312, organelle 304 is visible as a dark or opaque deposit 314.

Imaging of Oligonucleotide Hybridization

The assaying of the presence and concentration of specific-sequence oligonucleotides is nowadays typically being performed by the use of oligonucleotide probes of a complementary sequence attached to known locations on a substrate. Specific and widely used examples of such systems are the so-called DNA-chips. Such chips are surfaces bearing a plurality of oligonicleotide-probe sequences in known and discreet locations on a surface. A sample that may or may not contain the target sequences that complement the probe sequences on chip is treated so that all DNA fragments are labeled (usually by fluorescent labels). Contacting the sample with the surface of the chip under appropriate conditions, the target oligonucleotides attach to the surface in locations bearing the complementary sequence. Detection of hybridization products is usually done by following the fluorescence of labeled duplexes. The location of hybridization product indicates the sequence of the probe and fluorescence intensity indicates their surface concentration.

Figure 7:
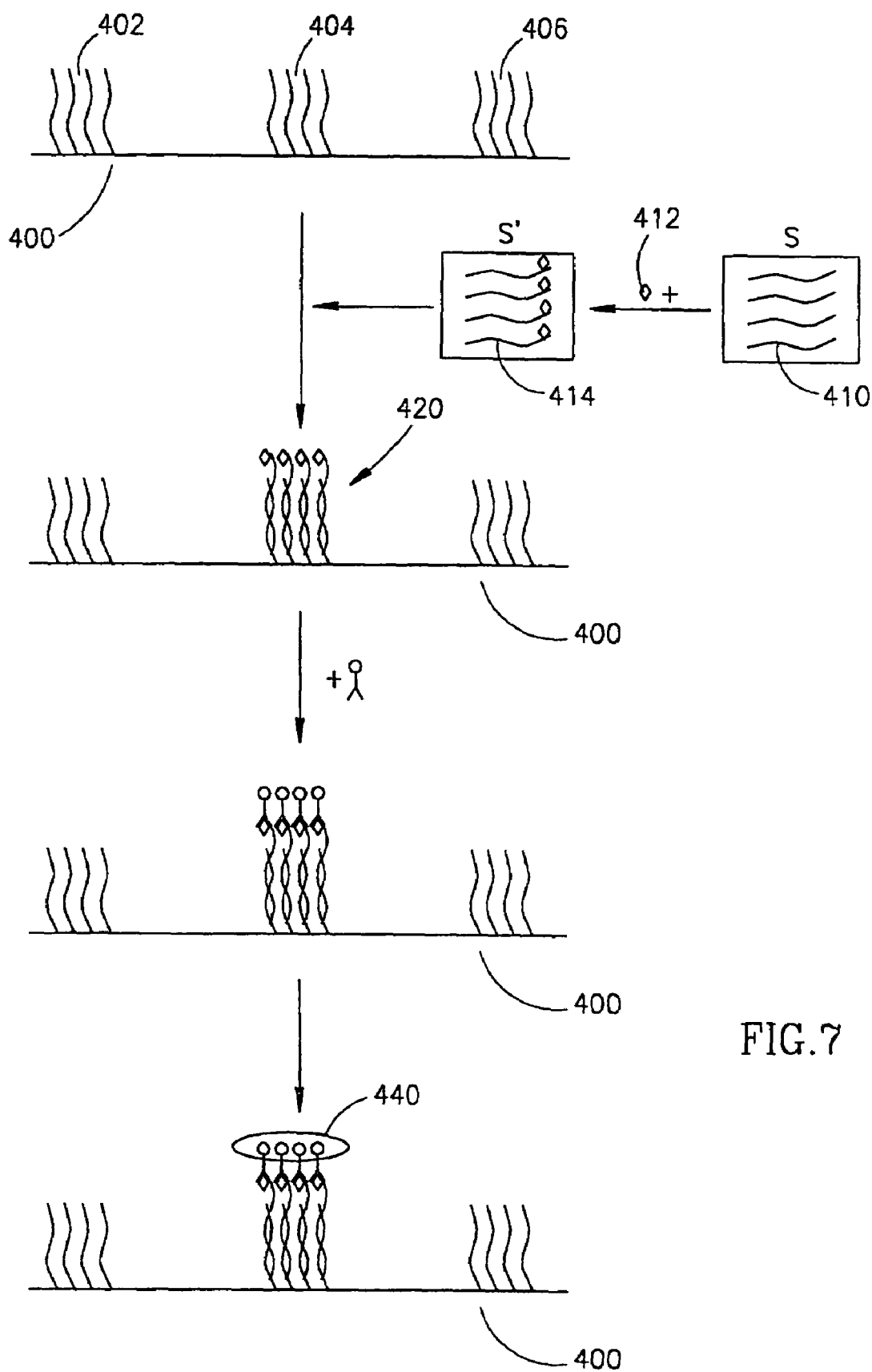
FIG. 7 shows the application of the system in the detection of analytes, oligonucleotides with a specific sequence in this specific example, in a sample.

Reference is now being made to FIG. 7 showing the application of the gold deposition method of the invention in visualization of hybridization products on a DNA-chip using different possible visualization techniques such as optical techniques (absorption, reflectance) and non optical visualization techniques (AMF, STM etc.). As no doubt will be appreciated, this is but an example to the use of the method of the invention for visualizing binding of targets to probes in general, e.g. binding of c-DNA strands to complementary strands, a binding of an antibody to an antigen and other types of recognition couples.

A DNA-chip substrate 400 carries a plurality of DNA probe sites, three 402, 404 and 406 being exemplified, each one having a different nucleotide sequence. A sample S that may contain the target oligonucleotides 410 is treated in a way that all DNA species in solution become labeled by label 412, thus obtaining modified sample S' that may contain modified analyte (if analyte was present in S). Contacting modified sample S' with DNA-chip substrate 400 under appropriate conditions allows selective hybridization of DNA probes on chip to target oligonucleotides if present in modified sample S'. After washing the chip, nucleation centers-forming agents 430 are introduced to the system under condition allowing their binding to labels 412 on labeled oligonucleotides if present at the different sites on chip. After washing, nucleation centers are present only at locations where hybridization between probes on chip and target from solution occurred. Visualization of hybridization is achieved by applying the gold deposition method of the invention, thus growing gold grains from the nucleation centers on-chip and detecting the gold 440 grains using different techniques such as optical techniques and SPM techniques (AFM, STM etc.).

In another embodiment, the label serves itself as a nucleation center. In such case, the step of attaching the nucleation center to the label is skipped.

The invention claimed is:

1. A method for assaying presence of a specific substance at sites on a substrate, comprising:
   (a) providing conditions allowing formation of nucleation centers on sites containing said substance;
   (b) contacting said substrate with a treatment composition comprising a reagent and a soluble gold-providing agent that is a gold-containing molecule or complex, the composition being kinetically stable such that upon such exposure gold metal is essentially not deposited on the substrate unless a nucleation center is present thereon, and in the presence of a nucleation center at said sites, gold atoms are released from said gold-providing agent and deposited onto said nucleation center to form gold metal deposits at said sites; and
   (c) detecting metallic gold deposits on said substrate, a gold deposit at a site on the substrate indicating presence of said substance at said site;
   wherein said gold-providing agent is $Au^I(SNC)_2^-$ or $KAu^I(SNC)_2$.

2. The method of claim 1, wherein step (a) comprises:
   (a1) providing nucleation center-forming agents which each comprise at least one moiety having specific binding affinity to said substance, said at least one moiety being coupled to one or more of the group consisting of a metal particle, a cluster containing metal atoms, and a metal-containing complex; and
   (a2) contacting said substrate with said agents.

3. The method of claim 2, wherein said moiety is included in one member of a recognition couple consisting of two molecules or complexes which specifically bind to one another, the other member included in or constituting said substance.

4. The method of claim 3, wherein said recognition couple is a member of the group consisting of an antigen and an antibody or an antibody derivative with an antigen-binding domain; sugar and a lectin; a receptor and a ligand; a nucleotide sequence and a complementary nucleotide sequence; a nucleotide sequence and its binding protein or other specific binding agent; biotin and avidin or streptavidin; cellulose or chitin and cellulose binding domain; said moiety being one of the recognition couple and said substance being or including the other.

5. The method of claim 1, comprising:
   (a') providing a sample that may comprise one or more target oligonucleotides having one or more specific target sequences;
   (b') contacting said substrate with the sample;
   wherein said substrate is carrying one or more probe oligonucleotides, each of said probe oligonucleotides having a probing sequence complementary to one of said target sequences;
   wherein said specific substance includes regions where said target oligonucleotides hybridize to said probe oligonucleotides and said nucleation centers are formed where said target oligonucleotides hybridize to said probe oligonucleotides; and
   wherein the presence of said one or more target oligonucleotides in the sample is thereby assayed.

6. The method of claim 5, wherein said step (b) comprises:
   (b1) treating said sample to bind a label to oligonucleotides in the sample;
   (b2) contacting said sample with said substrate; and
   (b3) contacting said substrate with a nucleation center-containing agent, capable of specific binding to said label.

7. The method of claim 5, wherein said step (b) comprises:
   (b1) treating said sample so as to bind nucleation centers to oligonucleotides present therein; and
   (b2) contacting said samples with said substrate.

8. The method of claim 1, wherein said nucleation center is a gold particle, a cluster containing gold atoms, or a gold-containing complex or molecules.

9. The method of claim 1, wherein said treatment composition is an aqueous solution.

10. The method of claim 9, wherein said reagent is quinone.

11. The method of claim 1, wherein said substrate is a specimen for viewing in an imaging or visualization technique.

12. The method of claim 11, wherein the detection technique is based on light.

13. The method of claim 11, wherein detection technique is based on light absorbance, light transmission, light reflectance, light scattering, or a combination of two or more of the foregoing.

14. The method of claim 11, wherein said detection is made by techniques selected from transmission electron microscopy, scanning electron microscopy, or atomic force microscopy.

15. The method of claim 11, wherein the specimen may be viewed in a microscope.

16. The method of claim 1, wherein said substrate contains separated fractions of a sample.

17. The method of claim 1, wherein the specific substance is a specific separation product; wherein the method is for identifying locations of said specific separation product on the substrate, wherein said substrate comprises said specific separation product; wherein the presence of gold on said substrate signifies the presence of said specific separation product on the substrate at a site where the gold is detected.

18. A method for assaying presence of an analyte in a sample comprising:
   (a) providing a substrate carrying capturing agents which bind said analyte;
   (b) contacting said substrate with said sample, whereby said analyte binds to said capturing agents;
   (c) providing conditions permitting formation of nucleation centers on sites of said substrate comprising said analyte;
   (d) contacting said substrate with a treatment composition comprising a soluble gold-containing molecule or complex and a reagent, the composition being kinetically stable such that gold is deposited on the substrate essentially only at sites thereof containing the nucleation centers; and
   (e) detecting metallic gold deposits on said substrate, indicative of the presence of said analyte in said sample;
wherein said gold-containing molecule or complex is $Au^I(SNC)_2^-$ or $KAu^I(SNC)_2$.

19. The method of claim 18, wherein step (c) comprises:
   (c1) providing nucleation center-forming agents which each comprise at least one moiety having specific binding affinity to said analyte, said at least one moiety being coupled to one or more of the group consisting of a metal particle, a cluster of metal atoms, and a metal-containing complex; and
   (c2) contacting said substrate with said agents.

20. The method of claim 19, wherein said analyte is one of a binding couple consisting of an antigen and an antibody or an antibody derivative with an antigen-binding domain; sugar and a lectin; a receptor and a ligand; a nucleotide sequence and a complementary nucleotide sequence; a nucleotide sequence and its binding protein or other specific binding agent; biotin and avidin or streptavidin; cellulose or chitin and cellulose binding domain; and said at least one moiety is the other of said binding couple.

21. The method of claim 18, wherein step (b) comprises:
   (b1) contacting said sample with nucleation centers, the nucleation centers being one or more of the group consisting of metal particles, cluster of metal atoms and metal-containing complexes or molecules, and providing conditions for coupling of said nucleation centers to the analyte if present in the sample, thus obtaining a modified sample containing modified analytes; and
   (b2) contacting said substrate with said modified analytes bound to said nucleation centers.

22. The method of claim 21, wherein said analyte is one of a binding couple consisting of an antigen and an antibody or an antibody derivative with an antigen-binding domain; sugar and a lectin; a receptor and a ligand; a nucleotide sequence and a complementary nucleotide sequence; a nucleotide sequence and its binding protein or other specific binding agent; biotin and avidin or streptavidin; cellulose or chitin and cellulose binding domain; and said capturing agent is the other of said binding couple.

23. The method of claim 18, wherein said capturing agents are carried on the substrate between electrodes such that gold deposited onto said nucleation centers in step (d) establishes an electrical contact between the electrodes; and wherein detection of the gold deposits in step (e) is performed by measuring current-potential relationship between the electrodes.

24. The method of claim 19, wherein said metal particle, cluster of metal atoms or metal-containing complex is a gold particle or cluster containing gold atoms.

25. The method of claim 18, wherein said treatment composition is an aqueous solution.

26. The method of claim 25, wherein said reagent is a hydroquinone.

* * * * *